US00PP21240P3

(12) United States Plant Patent
Philley et al.

(10) Patent No.: US PP21,240 P3
(45) Date of Patent: Aug. 24, 2010

(54) ST. AUGUSTINEGRASS PLANT NAMED 'POLARIS'

(50) Latin Name: *Stenotaphrum secundatum*
Varietal Denomination: Polaris

(75) Inventors: H. Wayne Philley, Mathiston, MS (US); Jeffrey V. Krans, Manitowish, WI (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 12/012,518

(22) Filed: Feb. 1, 2008

(65) Prior Publication Data

US 2009/0199316 P1 Aug. 6, 2009

(51) Int. Cl.
*A01H 5/00* (2006.01)

(52) U.S. Cl. ..... Plt./392

(58) Field of Classification Search ..... Plt./392
See application file for complete search history.

*Primary Examiner*—Annette H Para
(74) *Attorney, Agent, or Firm*—Lawrence Arthur Schemmel

(57) ABSTRACT

St. Augustinegrass plant 'Polaris' is a new and distinct variety of perennial St. Augustinegrass cultivar, characterized by its short and narrow leaf blades, fine leaf texture, short internode length and diameter, and superior cold tolerance and turf quality. 'Polaris' is also distinguished by its superior green plot and living ground cover characteristics.

6 Drawing Sheets

Latin name: *Stenotaphrum secundatum.*
Varietal denomination: 'Polaris'.

BACKGROUND OF THE INVENTION

This invention relates to a new and distinct perennial St. Augustinegrass variety adapted and suited for turfgrass applications. It is a high-quality cultivar well-suited for warm weather climates similar to that found in northern Mississippi and where high quality St. Augustinegrass grass cultivars have previously not been available. The Latin name of the genus and species of the novel cultivar disclosed is *Stenotaphrum secundatum*. This novel hybrid genotype has been given the varietal denomination 'Polaris' and is a perennial, asexually propagated genotype of St. Augustinegrass. St. Augustinegrass typically grows vigorously well in warm weather climates and spreads through creeping stolons that root at the nodes contacting soil with adequate moisture. Some commonly-known varieties of this genus and species include 'Raleigh' St. Augustine (not patented), 'Floratam' (not patented), 'B12' (U.S. Plant Pat. No. PP16,174 and marketed under the tradename 'Sapphire'™), and 'SS-100' (U.S. Plant Pat. No. PP9,395 and marketed under the tradename 'Palmetto'™). The designation 'Polaris' was evaluated under the experimental name 'MSA 2-3-98' and may also designate this plant in commerce. It is expected that the plant of this invention will be marketed under the synonym 'Polaris' St. Augustine as a tradename. The plant is identified interchangeably by its designation and its experimental name throughout this disclosure and its tables and figures. This high quality novel and distinct variety of St. Augustinegrass was vegetatively propagated at Starkville, Miss.

SUMMARY OF THE INVENTION

The cultivar 'Polaris' (experimental name 'MSA 2-3-98') is a distinctive, new variety of St. Augustinegrass characterized by its unique pedigree and very good cold tolerance and turf quality. The traits of the invention are continually maintained when propagated asexually. This new variety provides an appealing uniform, dense, dark green turf at locations where other St Augustinegrasses are weakened by winter and disease injury. 'Polaris' also exhibits other qualities and characteristics such as earlier spring green up and finer leaf texture than other St. Augustinegrass cultivars which allow it to be further distinguished from other cultivars.

BRIEF DESCRIPTION OF THE DRAWINGS

FIG. 1 is a flow chart diagram and graphical illustration of the unique pedigree of 'Polaris' showing the three generations of crossing of St. Augustinegrass genotypes resulting in the distinctive new cultivar.

DETAILED BOTANICAL DESCRIPTION OF THE VARIETY

Figure 2:
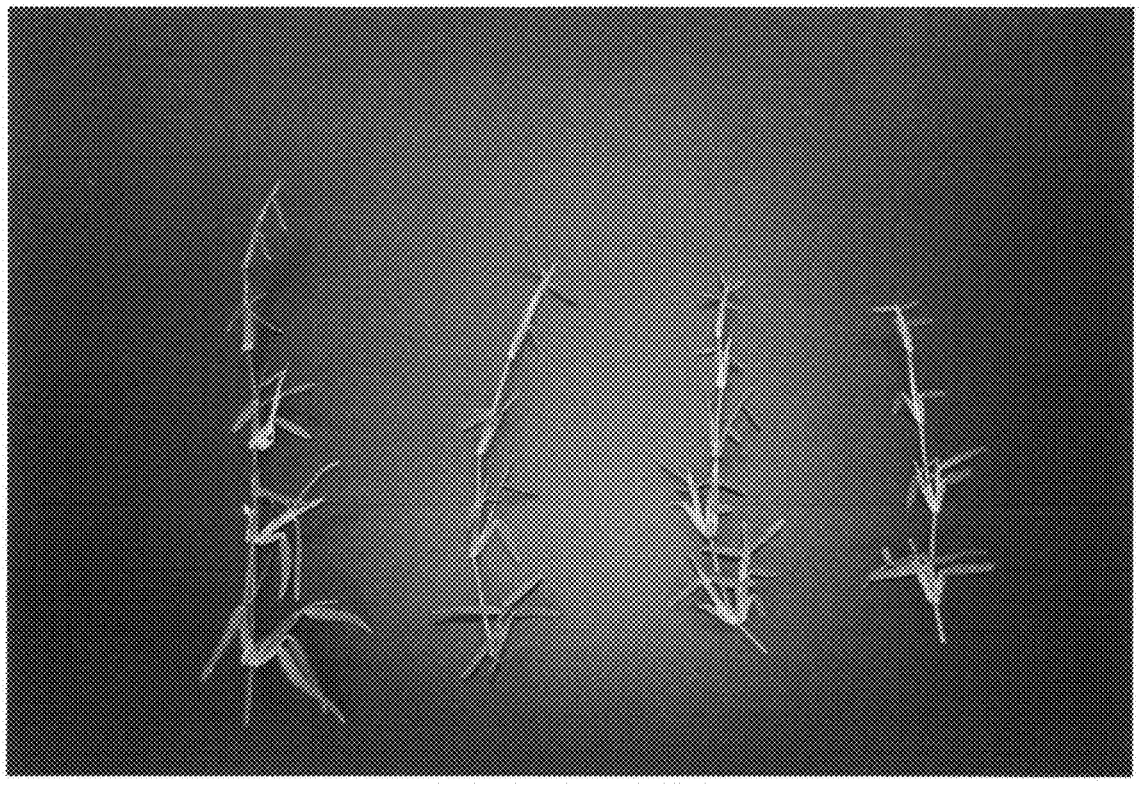
FIG. 2 is a color photograph taken on Apr. 24, 2006 at the Mississippi State University Department of Plant & Soil Sciences Dorman greenhouses of stolon segments of four (4) St. Augustinegrass cultivars that compares and illustrates the distinct morphologies of each segment. From left to right, 'Floratam' with its long leaves and purple internodes is shown on the far left. Next in line to the right is 'Raleigh' with its long leaves and green/yellow internodes. Next in line to the right is 'Polaris' with its small leaves and green internodes. Finally on the far right, 'MSA-31', an experimental cultivar, is shown with its small leaves and dark green internodes.

The following is a detailed botanical description of the characteristics of a new *Stenotaphrum secundatum* grass variety known as 'Polaris' (experimental name 'MSA 2-3-98'), based upon observations of the plant grown under conventional greenhouse conditions and in nursery pots and field plots at the Mississippi State University Mississippi Agricultural and Forestry Experiment Station in Oktibbeha County, Miss. Color notations of plant tissues are based upon the Munsell® Color Chart for plant tissues [*Munsell Book of Color: Glossy Finish Edition,* Munsell Color, Baltimore, Md., 1976; and *Munsell Color Charts for Plant Tissues*, Munsell Color, Baltimore, Md., 1977]. Color notations are affected by light quality and fertility and general plant growth. Certain characteristics will vary depending on the age of the plants, such that characteristics such as dimensions, sizes, and colors are approximations or averages since the variety has not been observed under every possible environmental condition. Therefore, the phenotype of the variety may differ from the descriptions depending upon environmental variations including but not limited to the season, temperatures, day lengths, light direction and quality, and fertilization, as well as other factors.

'Polaris' is a perennial, vegetatively (asexually) propagated genotype of St. Augustinegrass. The creeping or ascendant stolons of 'Polaris' are dorsiventrally compressed and root adventitiously at the nodes. Its leaf blade color is dark green and is rated 7.5 GY 4/4 based on a Munsell® Color Chart for plant tissue. The color chart match was completed with no supplemental lighting in a heated greenhouse in the month of December. 'Polaris' has a green internode color that is fairly stable, in contrast to the internodes of other St. Augustinegrass cultivars that may change to various shades of purple with cooler temperatures, such as 'Floratam' in particular. 'Polaris' typically has yellow anthers and white stigmas and has an unreduced chromosome number of 18.

Unique Pedigree and Origin of 'Polaris'

'Polaris' resulted from three generations of crossing among diploid St. Augustinegrass plants which were selected based upon winter survival ability and turf quality. One hundred-fifty-six (156) F1 plants (F1 refers to first generation) were generated from a diallel mating of eight (8) St. Augustinegrass genotypes with a wide range of cold tolerance. F2 plants (F2 refers to second generation) were generated by planned crossing of attractive F1 plants. Twenty-two (22) F2 plants were evaluated for winter survival ability and turf quality. One-hundred-sixty-one (161) F3 plants (F3 refers to third generation) were generated from planned crossing and open pollination of F2 plants. The new cultivar 'Polaris' resulted from open (possibly self) pollination of a second generation plant designated as F2-1. The original, single seed that produced 'Polaris' was germinated in a temperature-controlled germination chamber. The seedling was transplanted to a pot grown in a greenhouse and eventually transplanted to a field nursery. From that point in time forward, 'Polaris' has been vegetatively propagated and has consistently and completely been stably reproduced by the aforementioned asexual propagation. FIG. 1 shows the pedigree of 'Polaris' in a flowchart format. In FIG. 1, 'MSA-10' was a Mississippi St. Augustinegrass experimental cultivar from Mississippi State University (MSU) selected for winter survival. 'SATX 8262' was a St. Augustinegrass experimental cultivar from Texas A&M University also selected for winter survival. The unique origin of 'Polaris' shown distinguishes it from other commercially produced St. Augustinegrass varieties in that most of such varieties are of unknown origin. The pedigree of 'Polaris' is unique in that its parents and grandparents are known. The most cold tolerant varieties available were used in selecting both the first and second generation crosses used for the pedigree of 'Polaris'. As a result, 'Polaris' has equal or better cold tolerance than both its parents and grandparents and produces higher turf quality than both sets of ancestors.

Morphology of 'Polaris'

The morphological characteristics of 'Polaris' also distinguishes it from other St. Augustinegrass cultivars. To measure morphological characteristics, five (5) four-inch plugs of each of four (4) St. Augustinegrass cultivars were harvested from established field plots at Starkville, Miss. in March, 2006. These twenty (20) plugs were washed free of soil and transplanted to six-inch pots filled with commercial potting mix. These twenty (20) plugs were grown non-mown in a greenhouse for six (6) weeks before measurements were initiated. All stolons that grew out from the original plug were systematically evaluated, beginning with the youngest visible internode and proceeding backward toward the pot. Measurements included diameter and length of all internodes and width and length of all leaf blades.

Figure 3:
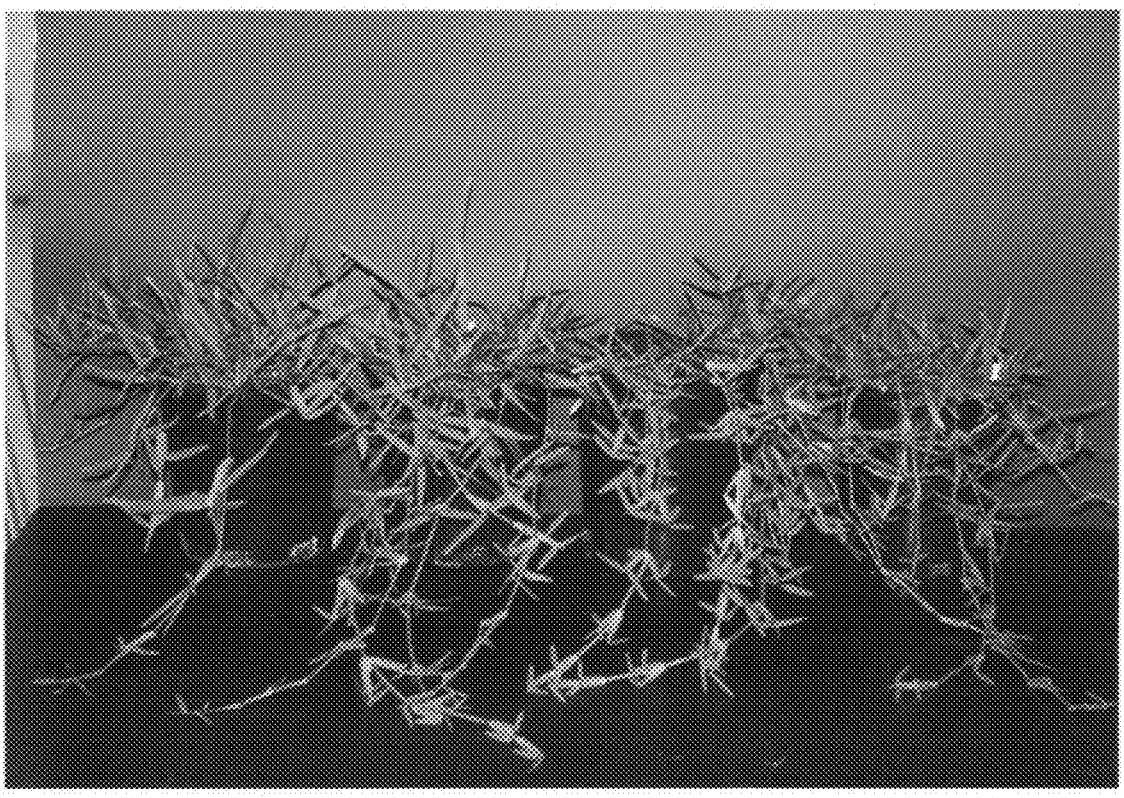
FIG. 3 is a color photograph taken on Apr. 24, 2006 at the Mississippi State University Department of Plant & Soil Sciences Dorman greenhouses of four (4) whole non-mown St. Augustinegrass cultivar plants in growing pots showing, from left to right: 'Floratam' with its longer leaves, tall stature, and purple/red internodes; 'Raleigh' with its longer leaves, tall stature, and green/yellow internodes; 'Polaris' with its smaller leaves, shorter stature, and more green internodes; and 'MSA-31' with its small leaves, shorter stature, and darker green internodes.

The non-mown leaf blade length of 'Polaris' was significantly shorter than that of cultivars 'Floratam' and 'Raleigh' but similar to MSU experimental cultivar 'MSA-31' (Table 1 and FIG. 2). FIG. 2 shows stolons of four (4) St Augustinegrass cultivars that illustrate different or comparative morphologies. FIG. 3 shows the same four cultivars as whole non-mown plants in growing pots. The leaf blade width of 'Polaris' was significantly narrower than 'Floratam' and 'Raleigh' and not significantly wider than 'MSA-31'. The internode length of 'Polaris' was significantly shorter than 'Floratam' and 'Raleigh' and significantly longer than 'MSA-31'. The internode diameter of 'Polaris' was significantly smaller than both 'Floratam' and 'Raleigh' and significantly larger than 'MSA-31'. 'Polaris' also differs visually from other cultivars in other respects. For example, 'Polaris's' yellow anthers and white stigmas are similar to some cultivars, such as the white stigmas of 'Raleigh' and 'Palmetto'™, but different from 'Palmetto'™'s and 'Floratam's' orange-yellow anthers, 'Floratam's' purple stigmas, and 'Sapphire'™'s gray-orange anthers and purple-violet stigmas.

The inflorescence of 'Polaris' is a spike-like raceme. The floral region of a mature inflorescence is 65–70 mm in length. Spikelets are embedded in one side of a thickened rachis. Spikelets are solitary or paired and positioned in two rows. When paired, one spikelet is borne on a 2–5 mm pedicel and the other is sessile. Each spikelet is ovoid and 4.0–4.5 mm in length. On each spikelet the outer glume is 1 mm in length, followed by two florets—one staminate and one fertile. The sterile lemma and palea and fertile lemma and palea are nearly equal in length (4.0–4.5 mm). 'Polaris' has white stigma color and yellow anther color and has not produced a seed, which is a highly desirable characteristic.

TABLE 1

Morphology measurements of St. Augustinegrass cultivars grown in non-mown pots.

| Cultivar | Leaf Blade Length mm | Leaf Blade Width mm | Internode Length mm | Internode Diameter mm |
|---|---|---|---|---|
| 'Floratam' | 63.9 | 8.9 | 62.2 | 3.54 |
| 'Raleigh' | 34.3 | 7.6 | 67.1 | 3.11 |
| 'Polaris' | 27.9 | 6.6 | 53.0 | 2.98 |
| 'MSA-31' | 27.9 | 6.5 | 49.0 | 2.48 |
| LSD (0.05) | 4.1 | 0.3 | 2.9 | 0.06 |

Turf Performance Evaluations

Turfgrass performance evaluation ratings in multiple tests likewise distinguish 'Polaris' from other St. Augustinegrass varieties.

Mississippi State University Test

Figure 4:
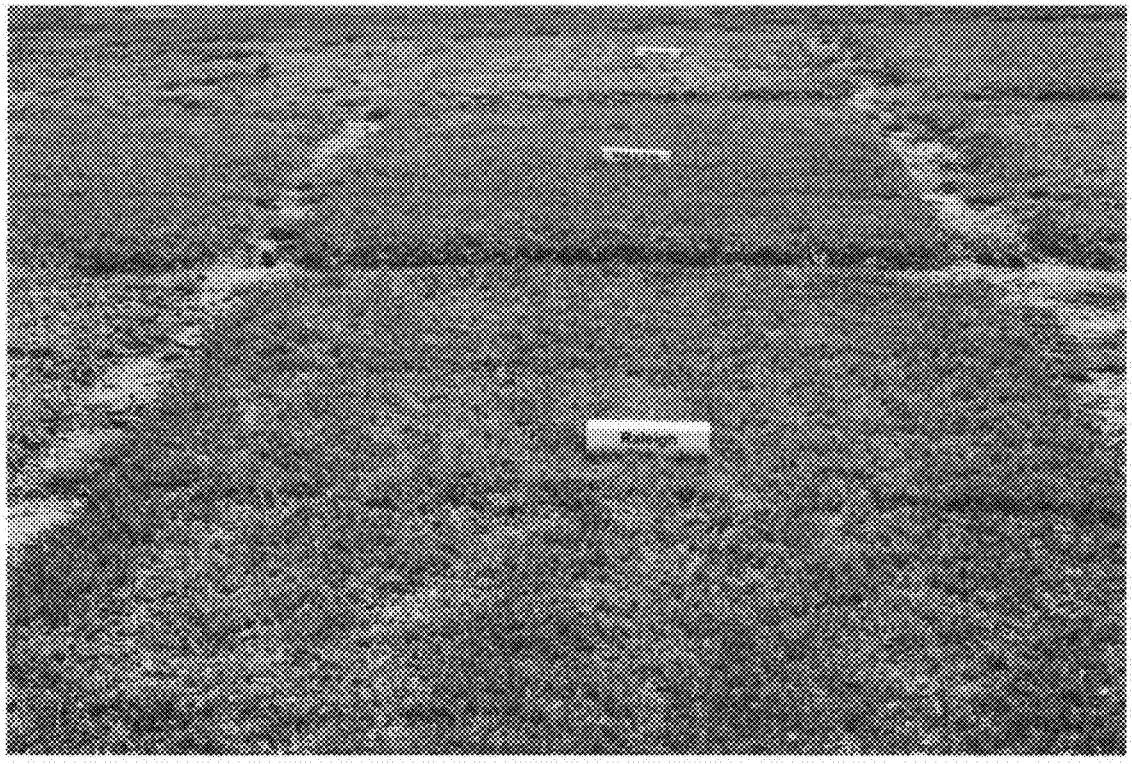
FIG. 4 is a color photograph taken on Mar. 30, 2005 at Starkville, Miss. showing field plots of three cultivars and specifically depicting the enhanced cold tolerance and winter survival of 'Polaris' St. Augustinegrass cultivar, as shown in the center, compared to the winter survival of 'Raleigh', a generally cold tolerant cultivar as shown in the foreground, and compared to the winter survival of 'Floratam', a generally cold susceptible cultivar as shown in the background.

'Polaris' was evaluated under the experimental name 'MSA 2-3-98' at the Mississippi State University Plant Science Research Center at Starkville, Miss. in the years 2000–2005. 'Polaris' and four (4) other F3 selections of experimental cultivars (third generation), along with standard cultivars 'Raleigh' and 'Floratam' and an experimental cultivar from the University of Florida, were planted in a randomized complete block design with three (3) replications. As shown in Tables 2 through 6, the 'MSA' cultivars were Mississippi St. Augustinegrass experimental cultivars from MSU. The 'FHSA' cultivar was a Florida Hawaii St. Augustinegrass experimental cultivar collected in Hawaii and tested at the University of Florida. 'Polaris' consistently ranked best for turf quality of all cultivars in the test (Table 2). The five-year spring green-up mean of 'Polaris' was higher than both 'Raleigh' and 'Floratam' and higher than three (3) of the experimental cultivars (Table 3). Leaf texture of 'Polaris' for a three-year average was rated finer than both 'Raleigh' and 'Floratam' and was rated finer than four (4) of the experimental cultivars (Table 4). 'Polaris' displayed moderate susceptibility to gray leaf spot disease in this test, but performed significantly better than five (5) of eight (8) cultivars in 2000 and six (6) of eight (8) cultivars in 2001, respectively (Table 5). Establishment rate of 'Polaris' was good and consistently ranked near the top for percent green plot cover compared to the other cultivars in the test (Table 6). Table 6 shows the establishment rate for two periods in 1999 and shows winter and disease injury recovery for two periods in 2001 and for 2005, respectively. FIG. 4 shows field plots of three (3) cultivars and the enhanced cold tolerance and winter survival of 'Polaris' (center) compared to 'Raleigh' (foreground), a generally cold tolerant cultivar, and 'Floratam' (background), a generally cold susceptible cultivar.

TABLE 2

Turf quality of a St. Augustinegrass test established at Misssissippi State University in 1999. (1 = poor, 9 = excellent).

| Cultivar | 2000 | 2001 | 2002 | 2003 | 2004 | 2005 | 2000-2005 |
|---|---|---|---|---|---|---|---|
| 'Polaris' | 7.9 | 7.7 | 7.2 | 7.1 | 7.1 | 7.2 | 7.4 |
| 'Raleigh' | 7.0 | 6.7 | 6.5 | 6.7 | 6.1 | 6.1 | 6.5 |
| 'MSA-10-4-98' | 7.0 | 6.4 | 6.7 | 6.6 | 6.1 | 5.8 | 6.4 |
| 'MSA-8-6-98' | 6.9 | 5.9 | 6.4 | 6.6 | 6.4 | 5.6 | 6.3 |
| 'MSA-13-6-98' | 5.6 | 6.0 | 5.3 | 5.9 | 5.9 | 4.6 | 5.5 |
| 'FHSA-115' | 5.6 | 4.7 | 5.3 | 5.4 | 5.8 | 4.9 | 5.3 |
| 'MSA-5-5-98' | 4.8 | 3.7 | 4.2 | 5.0 | 6.2 | 4.7 | 4.8 |
| 'Floratam' | 5.8 | 3.5 | 4.5 | 4.4 | 5.2 | 4.5 | 4.6 |
| LSD (0.05) | 0.7 | 1.2 | 1.1 | 0.9 | 0.7 | 1.0 | 0.4 |

TABLE 3

Spring green-up rating of a St. Augustinegrass test established at Mississippi State University in 1999. (1 = brown, 9 = completely green).

| Cultivar | 2000 | 2001 | 2002 | 2003 | 2004 | 2000-2004 |
|---|---|---|---|---|---|---|
| 'MSA-8-6-98' | 8.0 | 5.3 | 5.3 | 5.3 | 6.3 | 6.1 |
| 'MSA-13-6-98' | 7.3 | 6.0 | 5.7 | 5.0 | 6.0 | 6.0 |
| 'Polaris' | 7.7 | 5.3 | 4.7 | 5.3 | 6.3 | 5.9 |
| 'MSA-10-4-98' | 7.3 | 4.3 | 4.3 | 4.7 | 7.0 | 5.5 |
| 'Raleigh' | 6.0 | 5.7 | 4.0 | 5.0 | 5.6 | 5.3 |
| 'MSA-5-5-98' | 5.7 | 3.7 | 4.7 | 3.7 | 5.0 | 4.5 |
| 'FHSA-115' | 2.0 | 2.3 | 3.2 | 3.7 | 3.7 | 3.0 |
| 'Floratam' | 3.7 | 1.3 | 2.5 | 2.0 | 2.7 | 2.4 |
| LSD (0.05) | 0.8 | 1.4 | 1.0 | 1.2 | 0.8 | 0.4 |

TABLE 4

Leaf texture rating of a St. Augustinegrass test established at Mississippi State University in 1999. (1 = coarse, 9 = fine).

| Cultivar | 2000 | 2001 | 2003 | 3-year average |
|---|---|---|---|---|
| 'MSA-10-4-98' | 7.7 | 8.0 | 8.0 | 7.9 |
| 'Polaris' | 7.0 | 7.7 | 7.3 | 7.3 |
| 'MSA-8-6-98' | 7.3 | 7.0 | 7.0 | 7.1 |
| 'MSA-13-6-98' | 6.3 | 7.0 | 7.0 | 6.8 |
| 'MSA-5-5-98' | 6.3 | 6.7 | 7.0 | 6.7 |
| 'Raleigh' | 6.0 | 6.3 | 7.0 | 6.4 |
| 'FHSA-115' | 5.3 | 5.0 | 6.0 | 5.4 |
| 'Floratam' | 4.7 | 4.0 | 5.0 | 4.6 |
| Mean | 6.3 | 6.5 | 6.8 | 6.5 |
| LSD (0.05) | 0.9 | 0.6 | 0.4 | 0.4 |

TABLE 5

Gray leaf spot rating of a St. Augustinegrass test established at Mississippi State University in 1999. (1 = severe, 9 = no symptoms).

| Cultivar | Oct. 13, 2000 | Aug. 13, 2001 |
|---|---|---|
| 'Raleigh' | 5.3 | 7.2 |
| 'Polaris' | 5.3 | 6.7 |
| 'Floratam' | 6.3 | 4.7 |
| 'MSA-10-4-98' | 4.4 | 6.0 |
| 'FHSA-115' | 4.5 | 5.9 |
| 'MSA-8-6-98' | 3.8 | 5.6 |
| 'MSA-5-5-98' | 3.3 | 4.8 |
| 'MSA-13-6-98' | 2.1 | 4.7 |
| LSD (0.05) | 1.6 | 1.2 |

TABLE 6

Percent green plot cover of a St. Augustinegrass test established at Mississippi State University in 1999.

| | 1999[a] | | 2001[b] | | 2005[b] |
|---|---|---|---|---|---|
| Cultivar | Sep. 30 | Oct. 26 | May 4 | Aug. 13 | May 6 |
| 'FHSA-115' | 95.0% | 98.3% | 15.0% | 76.7% | 41.7% |
| 'Raleigh' | 88.3 | 96.7 | 85.0 | 98.3 | 50.0 |
| 'Polaris' | 85.0 | 95.0 | 81.7 | 100.0 | 73.3 |
| 'Floratam' | 76.7 | 83.3 | 2.3 | 48.3 | 33.3 |
| 'MSA-10-4-98' | 71.7 | 85.0 | 58.3 | 90.0 | 40.0 |
| 'MSA-8-6-98' | 70.0 | 81.7 | 61.7 | 88.3 | 46.7 |
| 'MSA-5-5-98' | 60.0 | 65.0 | 40.0 | 43.3 | 50.0 |
| 'MSA-13-6-98' | 36.7 | 41.7 | 80.0 | 90.0 | 60.0 |
| Mean | 72.9 | 80.8 | 53.0 | 79.4 | 48.8 |
| LSD (0.05) | 21.0 | 20.0 | 25.8 | 24.9 | NS |

[a]1999 data represents establishment rate.
[b]2001 and 2005 data reflect winter and disease injury.

Lawrenceburg, Tenn. Test

A St. Augustinegrass cultivar trial was conducted at the Lawrence County Extension Center at Lawrenceburg, Tenn. in the years 2002–2005. Eight (8) St. Augustinegrass cultivars, including 'Raleigh', 'Floratam', 'Polaris', and other experimental cultivars, were planted in a randomized complete block design with three (3) replications. 'Polaris' received the highest turf quality rating in each year of the test (Table 7). High percent green plot cover of 'Polaris' each spring comparatively demonstrated good winter survival capability (Table 8). Due to the severe winter of 2004–05, all test cultivars suffered winter injury as shown in the May 12, 2005 measurements of Table 8. However, as the Aug. 18, 2005 measurements of Table 8 show, 'Polaris' showed the highest recovery rate and percent green plot cover compared to all other cultivars tested, thereby confirming 'Polaris's' superior resiliency to cold temperatures. 'Polaris' displayed good turf density and color with little symptoms of gray leaf spot (Table 9). It demonstrated good color rating, the best turf density, and the best resistance to gray leaf spot disease of all the cultivars in the test.

TABLE 7

Turf quality of St. Augustinegrass test at Lawrenceburg, Tennessee. (1 = poor, 9 = excellent).

| Cultivar | 2002 | 2003 | 2004 | 2005 | 2002-2005 |
|---|---|---|---|---|---|
| 'Polaris' | 7.0 | 8.0 | 7.7 | 7.3 | 7.5 |
| 'MSA-10-4-98' | 6.7 | 7.3 | 7.6 | 6.0 | 6.9 |
| 'MSA-31' | 7.0 | 8.0 | 6.4 | 5.3 | 6.7 |
| 'Raleigh' | 6.0 | 7.3 | 6.5 | 5.7 | 6.4 |
| 'MSA-8-6-98' | 5.3 | 5.7 | 6.0 | 6.7 | 5.9 |
| 'MSA-5-5-98' | 5.3 | 4.7 | 5.3 | 5.3 | 5.2 |
| 'Floratam' | 4.7 | 4.3 | 4.2 | 2.3 | 3.9 |
| 'MSA-13-6-98' | 4.3 | 2.3 | 3.5 | 4.3 | 3.6 |
| LSD (0.05) | 1.2 | 2.2 | 2.2 | 2.2 | 1.6 |

TABLE 8

Percent green plot cover of St. Augustinegrass test at Lawrenceburg, Tennessee.

| Cultivar | May 18, 2003 | Nov. 13, 2003 | May 5, 2004 | May 12, 2005 | Aug. 18, 2005 |
|---|---|---|---|---|---|
| 'Polaris' | 95.0% | 100.0% | 70.0% | 25.0% | 91.7% |
| 'Raleigh' | 86.7 | 100.0 | 60.0 | 25.0 | 81.7 |
| 'MSA-10-4-98' | 71.7 | 95.0 | 50.0 | 6.7 | 81.7 |

TABLE 8-continued

Percent green plot cover of St. Augustinegrass test at Lawrenceburg, Tennessee.

| Cultivar | May 18, 2003 | Nov. 13, 2003 | May 5, 2004 | May 12, 2005 | Aug. 18, 2005 |
|---|---|---|---|---|---|
| 'MSA-8-6-98' | 70.0 | 66.7 | 56.7 | 38.3 | 76.7 |
| 'MSA-13-6-98' | 50.3 | 16.7 | 43.3 | 21.7 | 51.7 |
| 'MSA-5-5-98' | 46.7 | 56.7 | 43.3 | 35.0 | 68.3 |
| 'MSA-31' | 21.7 | 98.3 | 16.7 | 4.7 | 53.3 |
| 'Floratam' | 3.7 | 53.3 | 3.3 | 2.7 | 20.0 |
| LSD (0.05) | 35.7 | 32.2 | 27.1 | 20.3 | 33.9 |

TABLE 9

Color, density, and gray leaf spot ratings of the St. Augustinegrass test at Lawrenceburg, Tennessee rated on Aug. 18, 2005.

| Cultivar | Color | Density | Gray Leaf Spot[a] |
|---|---|---|---|
| 'Polaris' | 7.3 | 7.0 | 8.0 |
| 'MSA-31' | 7.7 | 6.0 | 5.0 |
| 'MSA-10-4-98' | 7.0 | 6.0 | 6.7 |
| 'Raleigh' | 6.7 | 5.7 | 7.0 |
| 'MSA-8-6-98' | 6.0 | 5.7 | 6.7 |
| 'Floratam' | 5.3 | 4.0 | 2.0 |
| 'MSA-5-5-98' | 6.0 | 3.7 | 5.7 |
| 'MSA-13-6-98' | 4.3 | 3.0 | 4.3 |
| LSD (0.05) | NS | 2.3 | 2.4 |

[a]Gray leaf spot rating scale: 1 = severe, 9 = no disease.
Color scale: 1 = light green, 9 = dark green
Density scale: 1 = low, 9 = high National Turfgrass Evaluation Program Test In order to further quantify its characteristics, 'Polaris' was entered under the experimental name 'MSA 2-3-98' into the 2002 National St. Augustinegrass Test coordinated by the National Turfgrass Evaluation Program (NTEP). This multiple-environment testing provided the best available and the most definitive data on the performance characteristics of 'Polaris' compared to other commercial and experimental St. Augustinegrass cultivars. The nine (9) test sites included Pomona, Calif.; Jay, Fla.; Griffin, Ga.; Savannah, Ga.; Calhoun, La.; Mississippi State, Miss.; Lane, Okla. Florence, S.C.; and College Station, Tex. Each site test included each variety listed in Tables 10 through 17. The specified experimental design at each site was a randomized complete block with three (3) replications of each variety tested. At each site, 'Polaris' was compared to 'Mercedes', 'Raleigh', 'Floratam', 'Delmar', and experimental cultivar 'MSA-31'.

'Polaris' consistently ranked at the top for turfgrass quality rating compared to all cultivars in each year of the NTEP test and ranked best in the 4-year mean turfgrass quality rating (Table 10). When averaged across all sites, 'Polaris' rated finer in leaf texture in each of three years than 'Raleigh', 'Delmar', and 'Floratam' (Table 11). 'Polaris' likewise displayed good genetic color (Table 12). Spring green-up ratings placed 'Polaris' better than both standard cultivars 'Raleigh' and 'Floratam' in each year (Table 13). Percent living ground cover estimates in spring placed 'Polaris' highest of all cultivars in the test in each of the three years (Table 14). At Lane, Okla., 'Polaris' suffered the least winterkill of all cultivars in the test in two out of three years tested (Table 15). 'Polaris' also displayed good resistance to take-all patch (Table 16). Turf quality and turf density ratings of 'Polaris' were good when grown under shade at Savannah, Ga. (Table 17).

TABLE 10

Turfgrass Quality ratings from 2002 National St. Augustinegrass Test. (1 = poor, 9 = excellent).

| Cultivar | 2002 | 2003 | 2004 | 2005 | 2002-2005 |
|---|---|---|---|---|---|
| 'Polaris' | 7.5 | 6.7 | 6.6 | 6.3 | 6.8 |
| 'MSA-31' | 7.5 | 6.5 | 6.3 | 5.8 | 6.5 |
| 'Mercedes' | 6.6 | 6.5 | 6.5 | 6.3 | 6.5 |
| 'Raleigh' | 6.3 | 6.3 | 6.0 | 6.0 | 6.2 |
| 'Floratam' | 6.3 | 6.4 | 5.9 | 5.7 | 6.1 |
| 'Delmar' | 5.7 | 6.1 | 6.0 | 5.8 | 5.9 |
| LSD | 0.3 | 0.4 | 0.3 | 0.4 | unavailable |

Note:
The 2002-2005 data is an average of the 4-year data.

TABLE 11

Leaf texture ratings from 2002 National St. Augustinegrass Test. (1 = coarse, 9 = fine).

| Cultivar | 2003 | 2004 | 2005 |
|---|---|---|---|
| 'MSA-31' | 5.2 | 4.8 | 5.8 |
| 'Polaris' | 4.7 | 4.6 | 5.3 |
| 'Mercedes' | 5.2 | 4.5 | 5.1 |
| 'Raleigh' | 4.5 | 3.9 | 4.4 |
| 'Delmar' | 4.6 | 3.5 | 4.3 |
| 'Floratam' | 3.7 | 3.0 | 3.5 |
| LSD | 0.5 | 0.4 | 0.5 |

TABLE 12

Generic color ratings from 2002 National St. Augustinegrass Test. (1 = light green, 9 = dark green).

| Cultivar | 2003 | 2004 | 2005 |
|---|---|---|---|
| 'Mercedes' | 6.4 | 7.7 | 5.9 |
| 'Polaris' | 6.5 | 7.4 | 6.1 |
| 'MSA-31' | 6.6 | 7.3 | 5.9 |
| 'Delmar' | 6.8 | 7.2 | 5.8 |
| 'Raleigh' | 6.4 | 7.0 | 5.4 |
| 'Floratam' | 6.7 | 6.4 | 5.5 |
| LSD | 0.5 | 0.4 | 0.5 |

TABLE 13

Spring green-up ratings from 2002 National St. Augustinegrass Test. (1 = brown, 9 = completely green).

| Cultivar | 2003 | 2004 | 2005 |
|---|---|---|---|
| 'Mercedes' | 5.5 | 4.6 | 4.8 |
| 'Delmar' | 5.3 | 4.5 | 4.6 |
| 'Polaris' | 5.3 | 4.2 | 4.9 |
| 'Raleigh' | 5.1 | 4.0 | 4.3 |
| 'MSA-31' | 4.0 | 3.9 | 3.9 |
| 'Floratam' | 3.9 | 3.6 | 3.2 |
| LSD | 0.5 | 0.4 | 0.5 |

TABLE 14

Percent living ground cover in spring from 2002 National St. Augustinegrass Test.

| Cultivar | 2003 | 2004 | 2005 |
|---|---|---|---|
| 'Polaris' | 67.3% | 90.3% | 79.9% |
| 'Mercedes' | 64.2 | 89.2 | 78.2 |
| 'Raleigh' | 64.5 | 88.3 | 77.1 |

TABLE 14-continued

Percent living ground cover in spring from 2002 National St. Augustinegrass Test.

| Cultivar | 2003 | 2004 | 2005 |
|---|---|---|---|
| 'Delmar' | 51.8 | 87.3 | 75.0 |
| 'MSA-31' | 51.4 | 74.7 | 49.3 |
| 'Floratam' | 48.8 | 64.5 | 51.1 |
| LSD | 7.3 | 4.4 | 8.1 |

TABLE 15

Percent winterkill in Lane, Oklahoma.

| Cultivar | 2003 | 2004 | 2005 |
|---|---|---|---|
| 'Floratam' | 43.3% | 80.0% | 63.3% |
| 'MSA-31' | 16.7 | 53.3 | 80.0 |
| 'Raleigh' | 8.3 | 30.0 | 36.7 |
| 'Mercedes' | 20.0 | 30.0 | 36.7 |
| 'Delmar' | 16.7 | 23.3 | 23.3 |
| 'Polaris' | 6.7 | 23.3 | 40.0 |
| LSD | 7.1 | 11.4 | 13.7 |

TABLE 16

Take-all patch rating at Lane, Oklahoma in 2004.

| Cultivar | Rating[a] |
|---|---|
| 'Floratam' | 7.3 |
| 'Polaris' | 7.0 |
| 'Delmar' | 6.0 |
| 'Raleigh' | 5.7 |
| 'MSA-31' | 4.3 |
| 'Mercedes' | 4.0 |
| LSD | 0.9 |

[a]Disease rating: 1 = severe, 9 = no disease

TABLE 17

Turf quality and density ratings at Savannah, Georgia under shade. (Quality: 1 = poor, 9 = excellent) (Density: 1 = low, 9 = high)

| | Quality | | | Density | | |
|---|---|---|---|---|---|---|
| Cultivar | 2003 | 2004 | 2005 | 2003 | 2004 | 2005 |
| 'MSA-31' | 7.2 | 7.6 | 7.6 | 7.7 | 8.3 | 6.0 |
| 'Polaris' | 6.3 | 7.4 | 7.8 | 6.7 | 6.5 | 7.5 |
| 'Raleigh' | 6.6 | 7.5 | 6.8 | 7.1 | 7.0 | 6.3 |
| 'Mercedes' | 6.0 | 6.9 | 6.8 | 6.3 | 6.7 | 5.3 |
| 'Delmar' | 5.5 | 7.1 | 6.8 | 5.9 | 6.3 | 6.3 |
| 'Floratam' | 4.7 | 5.5 | 5.3 | 4.9 | 5.7 | 3.3 |
| LSD | 0.9 | 0.7 | 1.1 | 1.2 | 1.7 | 1.6 |

SUMMARY

Observations and analyses on a comparative basis identified characteristics of 'Polaris' that distinguish it from other St. Augustinegrasses including 'Raleigh', 'Floratam', 'Mercedes', 'Delmar', and various experimental cultivars. In particular, the superior cold tolerance and turf quality of 'Polaris' allows it to be produced, marketed, and commercialized as a higher quality St. Augustinegrass capable of surviving cold temperatures and winter seasons in northern Mississippi and in United States Department of Agriculture (USDA) plant hardiness zone 7 and higher. Its superior percent green plot cover and living ground cover ratings provide further distinctions and advantages compared to other St. Augustinegrass cultivars.

As will be apparent to those skilled in horticultural science, the new and distinct perennial St. Augustinegrass variety described herein may vary in minor detail due to climatic, soil, and cultural conditions under which the variety may be grown, as well as the stage of growth.

Comparative DNA Analysis of 'Polaris' with other Turfgrasses

Randomly Amplified Polymorphic DNA (RAPD) analysis was used to generate DNA fingerprints that uniquely identified 'Polaris' from other St. Augustinegrasses. All tests and analyses were performed by Juliet D. Tang, Life Sciences and Biotechnology Institute (Mississippi State University).

The sequence identifiers listing is also included in an ASCII text format file on CD-R disc and is incorporated herein by reference. The file name is polaris3.txt created on May 26, 2009 and is 530 bytes in file size.

Plants

St. Augustinegrasses were obtained from Wayne Philley at Mississippi State University. Six turfgrass varieties were tested: 'Sapphire'™, 'Raleigh', 'Polaris', 'MSA 31', 'Palmetto'™, and 'Floratam'. Grasses were grown individually in pots in the Institute greenhouse. One block consisted of each plant variety and each block was replicated four (4) times.

DNA Isolation

DNA was extracted from young leaf blades according to the DNeasy Plant Mini Kit Protocol sold by Qiagen Inc. (Valencia, Calif.). Plant tissue (100 mg) was pulverized in liquid N2 using a mortar and pestle. Negative controls were subjected to the same procedures, except no plant tissue was added. After extraction, the DNA concentration was determined and all samples were diluted to the same working concentration.

Amplification Primers

Eighty-five ten-mer primers were purchased from Operon Biotechnologies, Inc. (Huntsville, Ala.). Forty-four primers (OPA9, OPAA15, OPAA16, OPAB2, OPAC2, OPAC3, OPAC10, OPAC11, OPAC20, OPAE6, OPAF7, OPAG17, OPAH20, OPAI18, OPAN6, OPAO5, OPAP15, OPAT13, OPAU1, OPAV1, OPAX9, OPB4, OPB9, OPB10, OPB12, OPB15, OPB17, OPBA9, OPBE8, OPBE17, OPBG2, OPC4, OPC8, OPC11, OPC12, OPE2, OPH4, OPJ10, OPK4, OPM5, OPP15, OPP19, OPW15, OPY20) produced DNA fragments that were polymorphic, i.e. band(s) present in one variety and absent in another when tested against one block of grass DNA. Fifteen of these primers (OPA9, OPAC2, OPAC20, OPAH20, OPAI18, OPAU1, OPAX9, OPB4, OPB9, OPB12, OPBA9, OPC4, OPE2, OPH4, OPM5) were then tested against all four blocks of grass DNA. 'Polaris' was uniquely identified across all four replicates when the fingerprints of primers OPAU1 and OPAC20 were considered together. An example fingerprint for each primer is exhibited in FIGS. 5 and 6, respectively.

Amplification

Primer-specific amplification of DNA was performed using Takara Taq DNA polymerase (Takara Mirus Bio, Madison, Wis.), the manufacturer's supplied buffer, and 2.5 mM $MgCl_2$ in a polymerase chain reaction (PCR). The hot start method of preheating the DNA (25 ng) five minutes at 95 deg Celsius (C.) prior to the addition of the enzyme-primer master mix was employed. All amplifications were placed in a MyCycler thermal cycler (Bio-Rad, Hercules, Calif.) and run with the following program:

1. 2 min at 95 deg C.
2. 30 s at 94 deg C.
3. 1 min at 35 deg C.
4. 2 min at 72 deg C.
5. return to step 2 and cycle 45 times
6. 20 min hold at 60 deg C.
7. infinite hold at 4 deg C.

Gel Electrophoresis and Photography

DNA fragments produced by PCR were separated on a 1.5% agarose gel in Tris-acetate-EDTA buffer, then stained with $EtBr_2$, and visualized using a Versadoc 3000 (Bio-Rad, Hercules, Calif.). The lanes of the gel photographs, shown in FIGS. 5 and 6, correspond to (from left to right): Lane 1='Sapphire'™, Lane 2='Raleigh', Lane 3='Polaris', Lane 4='MSA 31', Lane 5='Palmetto'™, Lane 6='Floratam', Lane 7=negative control, and Lane 8=100 bp PCR molecular ruler size marker (Bio-Rad, Hercules, Calif.).

RAPD Analysis

Figure 5:
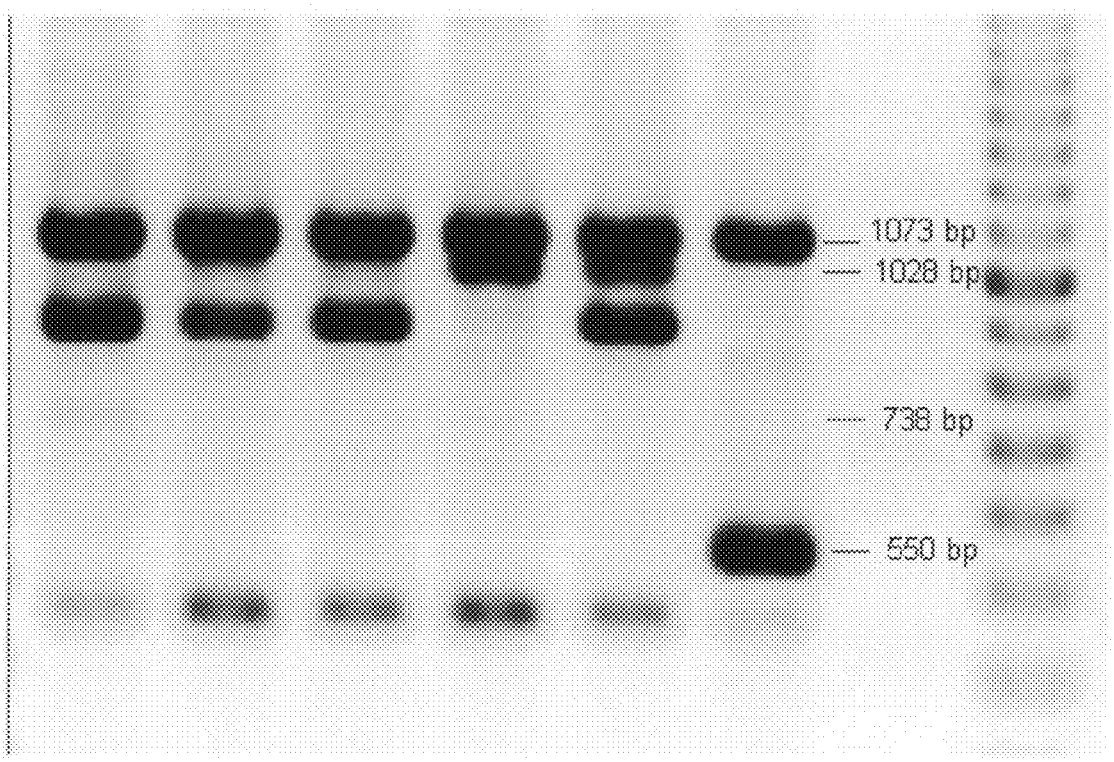
FIG. 5 is a photograph of the unique DNA amplification profile of 'Polaris' and the DNA profiles of five (5) other St. Augustinegrass cultivars using RAPD primer OPAU1, illustrating that 'Polaris' is different from 'Sapphire'™, 'MSA 31', 'Palmetto'™, and 'Floratam'.
Figure 6:
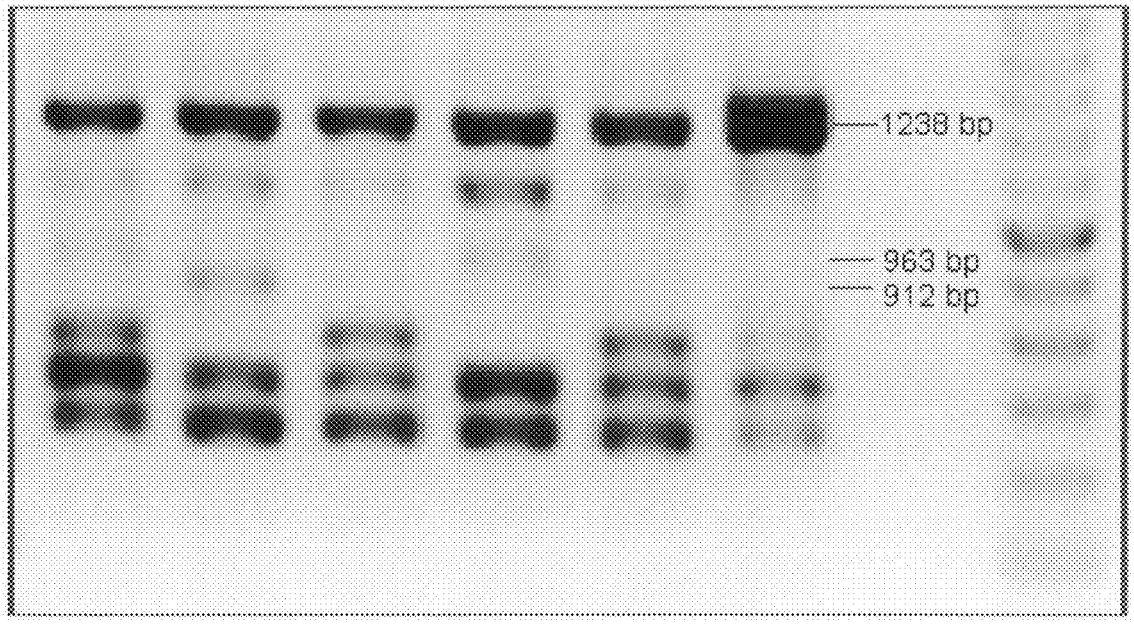
FIG. 6 is a photograph of the unique DNA amplification profile of 'Polaris' and the DNA profiles of five (5) other St. Augustinegrass cultivars using RAPD primer OPAC20, illustrating that 'Polaris' is different from 'Raleigh', 'Sapphire'™, 'MSA 31', and 'Floratam'.

For RAPD analysis, bands in the gel images were detected, matched, and sized using QuantityOne software, (Bio-Rad, Hercules, Calif.). All samples could be distinguished from the others using one or more of the ten-mer primers. As shown in FIG. 5, 'Polaris' (Lane 3) shows absences of three bands at 1028 bp, 738 bp, and 550 bp when tested with primer OPAU1. Absence of the 738 bp band differentiates 'Polaris' from 'Sapphire'™ (Lane 1). Absence of the 1028 bp band differentiates 'Polaris' from 'MSA 31' (Lane 4) and 'Palmetto'™ (Lane 5). Absence of the 550 bp band differentiates 'Polaris' from 'Floratam' (Lane 6). As shown in FIG. 6, 'Polaris' (Lane 3) shows absences of the 963 bp and 912 bp bands when tested with primer OPAC20. Absence of the 912 bp band differentiates 'Polaris' from 'Raleigh' (Lane 2). Absence of the 963 bp band differentiates 'Polaris' from 'Sapphire'™ (Lane 1) and 'MSA 31' (Lane 4). Fewer copies of the 1238 bp band differentiates 'Polaris' from 'Floratam' (Lane 6).

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
```

-continued

```
<223> OTHER INFORMATION: Primer OPAU1

<400> SEQUENCE: 1

gggatggaac                                                          10


<210> SEQ ID NO 2
<211> LENGTH: 10
<212> TYPE: DNA
<213> ORGANISM: Artificial Sequence
<220> FEATURE:
<223> OTHER INFORMATION: Primer OPAC20

<400> SEQUENCE: 2

acggaagtgg                                                          10
```

What is claimed is:

1. A new and distinct variety of perennial St. Augustinegrass plant, substantially as herein illustrated and described.

* * * * *

('MSA-10') x ('SATX 8262')
↓
(F1-16)

('Raleigh') x ('MSA-10')
↓
(F1-24)

x
↓
(F2-1)

x open-pollinated
↓
('MSA 2-3-98')

Figure 1

'Floratam' 'Raleigh' 'MSA 2-3-98' 'MSA-31'

'Floratam' 'Raleigh' 'MSA 2-3-98' 'MSA-31'